United States Patent [19]

Hattori

[11] Patent Number: 4,563,583
[45] Date of Patent: Jan. 7, 1986

[54] SCINTILLATION CAMERA
[75] Inventor: Hiroyuki Hattori, Kyoto, Japan
[73] Assignee: Shimadzu Corporation, Japan
[21] Appl. No.: 478,011
[22] Filed: Mar. 23, 1983
[30] Foreign Application Priority Data
Mar. 31, 1982 [JP] Japan .................................. 57-52870
[51] Int. Cl.⁴ ........................ G01T 1/208; G21K 1/02
[52] U.S. Cl. .............................. 250/363 S; 250/505.1
[58] Field of Search .......................... 250/363 S, 505.1; 378/147

[56] References Cited
U.S. PATENT DOCUMENTS
4,047,037 9/1977 Schlosser et al. ................... 250/370

OTHER PUBLICATIONS
W. Mauderli, R. W. Luthmann, L. T. Fitzgerald, M. M. Urie, C. M. Williams, C. W. Tosswill and G. Entine, "A Computerized Rotating Laminar Radionuclide Camera", *J. Nucl. Med.*, vol. 20, No. 4, (1979), pp. 341–344.
W. I. Keyes, "The Fan-Beam Gamma Camera", *Phys. Med. Biol.*, vol. 20, No. 3, (1975), pp. 489–493.

Primary Examiner—Alfred E. Smith
Assistant Examiner—Constantine Hannaher
Attorney, Agent, or Firm—Griffin, Branigan, & Butler

[57] ABSTRACT

In a scintillation camera with a position calculation circuit which is indispensable to the Anger scintillation camera, the number of incident gamma rays is integrated only in the lengthwise direction of the shielding plates of a rotatable parallel plate collimator. Data on one-dimensional distribution, which are collected every time the collimator has rotated by the specified angle, are subjected to image information processing so that a picture of distribution of gamma rays may be obtained. In the presently proposed improvements in the Anger scintillation camera, a coordinate transformation circuit is added thereto, in which outputs taken from a position calculation circuit in the form of data on two-dimensional distribution are transformed into data on one-dimensional distribution and fed to an arithmetic unit for the reconstruction of an image. A collimator, which is effective for the collection of data on one-dimensional distribution, is also proposed.

8 Claims, 17 Drawing Figures

SCINTILLATION CAMERA

BACKGROUND OF THE INVENTION

The present invention relates to a scintillation camera for obtaining a picture of distribution of a radioactive isotope (RI).

Conventional scintillation cameras, which were developed by H. 0. Anger and are in common use today, have the disadvantage that they cause the images to be distorted and that they are not sensitive enough.

Figure 1:
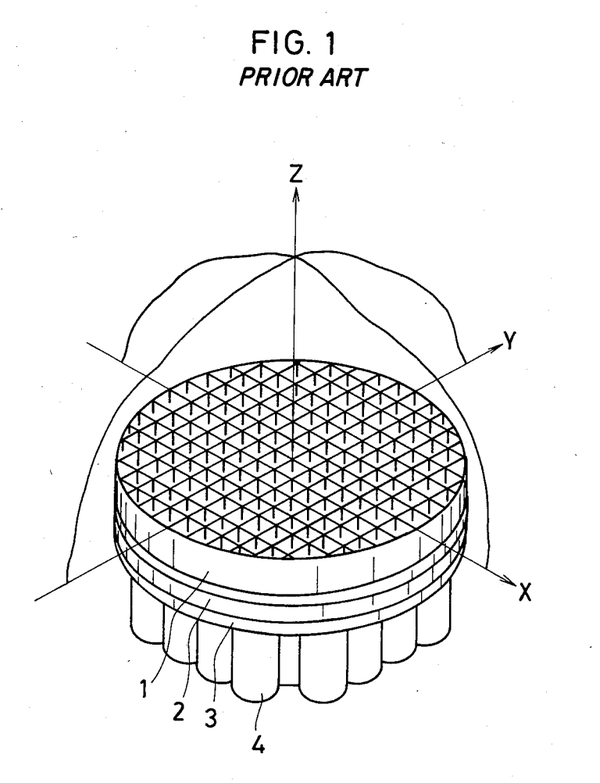
FIG. 1 is a perspective view of a conventional scintillation camera provided with a lattice type collimator.
Figure 2:
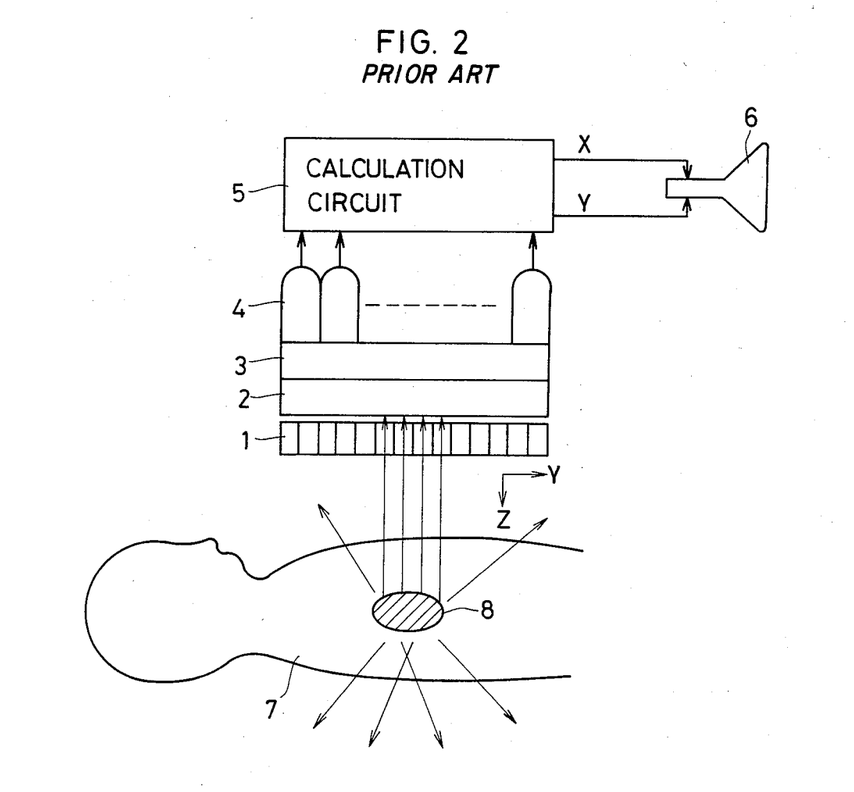
FIG. 2 is a schematic block diagram thereof.
Figure 3:
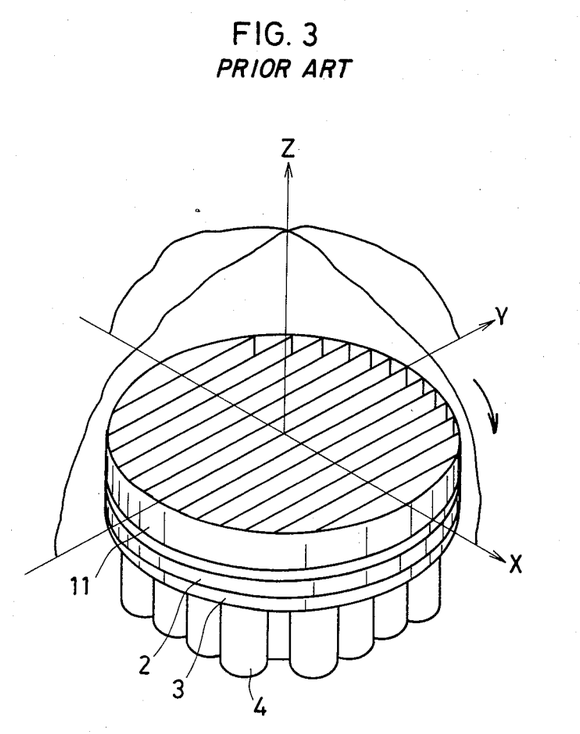
FIG. 3 is a perspective view of a conventional scintillation camera provided with a rotatable collimator.
Figure 4:
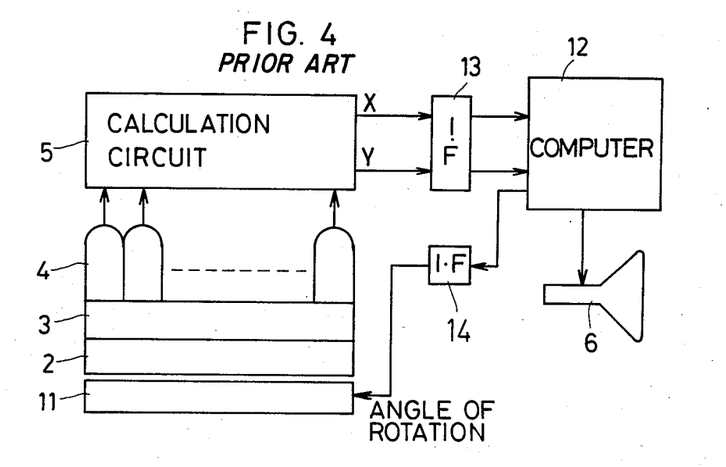
FIG. 4 is a schematic block diagram thereof.
Figure 5:
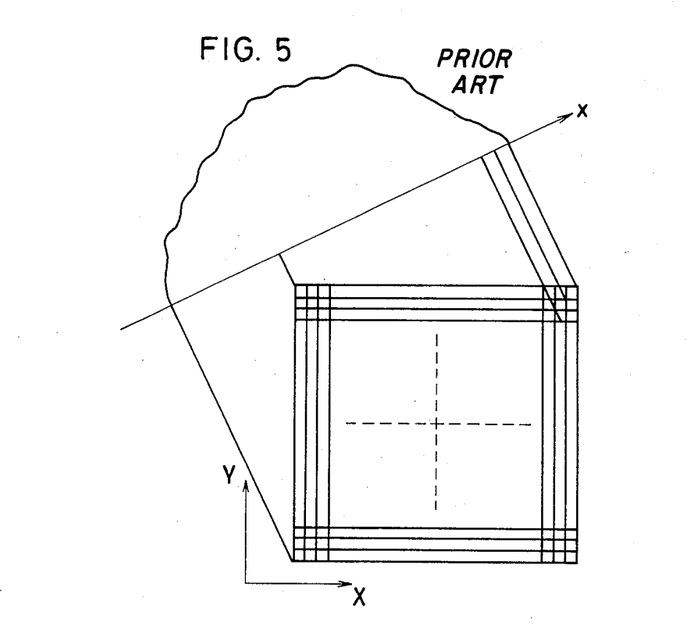
FIG. 5 is a memory map in which the outputs of a position calculation circuit provided in a conventional scintillation camera are listed.

One of two representative types of the Anger scintillation camera is equipped with a lattice type collimator as shown in FIGS. 1 and 2, while the other is equipped with a parallel plate collimator which is rotatable in construction as shown in FIGS. 3 to 5.

In the case of the scintillation camera shown in FIGS. 1 and 2, radioactive rays are collimated by the lattice type collimator 1 so that only those which are incoming perpendicularly to the surface of a flat type scintillator 2 (i.e., which are incoming in the direction of the Z axis) may be fed to the scintillator 2. A plurality of photomultipliers 4 arranged on the back of the scintillator 2 emit outputs which correspond to the scintillations of light applied to the photomultipliers through optical couplings or light guides 3. These outputs are fed to a position calculation circuit 5, in which the positions of scintillations (i.e., the positions on which the gamma rays are incident) are calculated from these outputs so that position signals X and Y may be developed. In a display unit 6, dots are displayed in the positions determined by the position signals X and Y. These dots gather in the picture and indicate a distribution of RI as it is viewed in the direction of the Z axis. Thus the specific organ 8 of a subject 7, in which RI is allowed to collect, can be diagnosed.

The trouble is that radioactive rays are emitted from the RI in all directions, and therefore it is not too much to say that gamma rays are not being efficiently utilized if they are admitted into a scintillation camera only from a single direction. In order that a scintillation camera may be highly sensitive, not only the gamma rays which are incoming in the direction of the Z axis but also those which are incoming in the oblique direction, have to be detected by the scintillator 2, not to speak of those which are incoming in the direction of the Z axis but are obstructed by the thickness of the strips of which the lattice type collimator 1 is made. This requirement is met by a rotating-collimator type scintillation camera.

The rotating-collimator type scintillation camera can be constructed from an ordinary scintillation camera. For this purpose, the lattice type collimator 1 (FIG. 1) is replaced by a parallel plate collimator 11 (FIG. 3) which is rotatably held, adapted to be rotated by a suitable mechanism, and connected to a computer 12 through interface circuits 13 and 14 as shown in FIG. 4. The angle of piecemeal rotation is specified by the computer 12. Every time the collimator 11 has rotated by the specified angle, signals X and Y are taken into the computer 12 and stored in the memory circuit thereof. On the other hand, the signals X and Y developed by the position calculation circuit 5 of the scintillation camera are listed as the picture elements of a two-dimensional matrix (FIG. 5). Since the coordinate axes of this matrix cannot be resolved, coordinate transformation is required for obtaining data on one-dimensional distribution from the abovedescribed data on two-dimensional distribution. Let it be supposed that that the X axis of the collimator 11 points to the direction of the arrow x as shown in FIG. 5. Then the angular difference between the X axis of the collimator 11 and that of the matrix is calculated by the computer 12 so that coordinate transformation may be effected by making necessary addition to the discrete value for each picture element defined by the X axis of the matrix. Thus a large number of data on one-dimensional distribution are obtained, which are subjected to image information processing so as to be reconstructed into a two-dimensional image. In order to improve the accuracy of a reconstructed image, the two-dimensional matrix must be sufficiently fine-meshed and the collimator 11 must be adapted to be rotated by as small angular distances as possible so that data on one-dimensional distribution may be obtained in as great numbers as possible. Let it be supposed that, in order to meet this requirement, data on one-dimensional distribution are going to be obtained from a two-dimensional matrix having a mesh size of $512 \times 512$ every time the collimator 11 rotates by 0.5 degree in the course of 180-degree rotation. Then, two-dimensional data on 360 pictures in the original coordinate system must be stored, which means that the number of memory locations required will amount to as large as $512 \times 512 \times 360$ and that the operation for the abovementioned coordinate transformation will place a large burden on the computer 12.

Under these circumstances, the first object of the present invention is to provide a scintillation camera which is based on a different principle from that of the conventional scintillation cameras and into which a computerized technique of image information processing is introduced so as to free the images from distortion and allow the camera to be highly sensitive and to have a high practical spatial resolution.

The second object of the present invention is to improve the Anger scintillation camera so as to make the high accuracy of reconstructed images compatible with a smaller number of data to be stored and thereby simplify the computer operation to such an extent that the time interval from the instant the operation is started until the instant an image is delivered may be reduced.

The third object of the present invention is to provide an anisotropic collimator for use in a scintillation camera, ECT, or the like, this collimator being of such simplified construction that a collimator having any degree of effectiveness as a field stop can be easily manufactured.

SUMMARY OF THE INVENTION

The first object of the present invention is accomplished by providing a parallel plate collimator which consists of a first set of shielding plates arranged in parallel with each other with regular spaces left between adjacent plates and a second set of shielding plates disposed at both ends and in the middle portion of the first set of shielding plates so as to intersect them, said collimator being rotatably disposed on the front side of a radiation detector provided with scintillators, by providing a means by which the number of incident gamma rays is integrated in the lengthwise direction of the first set of shielding plates and, every time the collimator has rotated by a very small angle, data on the distribution of these integrated counts rates are collected in the direction perpendicular to the longitudinal edges of the first set of shielding plates, and by providing an arithmetic unit for the reconstruction of an image.

The second object of the present invention is accomplished by providing a position calculation circuit from which outputs are taken in the form of data on two-dimensional distribution, by providing a coordinate transformation circuit in which these data on two-dimensional distribution are transformed into data on one-dimensional distribution, and by providing an arithmetic unit for the reconstruction of an image.

The third object of the present invention is accomplished by providing a plurality of equally spaced parallel plates having a pronounced property of absorbing gamma rays, and by providing a corrugated spacer which is inserted into each space between adjacent parallel plates and is inferior to the parallel plates in the property of absorbing gamma rays.

DESCRIPTION OF THE PREFERRED EMBODIMENTS

Preferred embodiments of the present invention are hereinafter described in detail with reference to the accompanying drawings.

Figure 6:
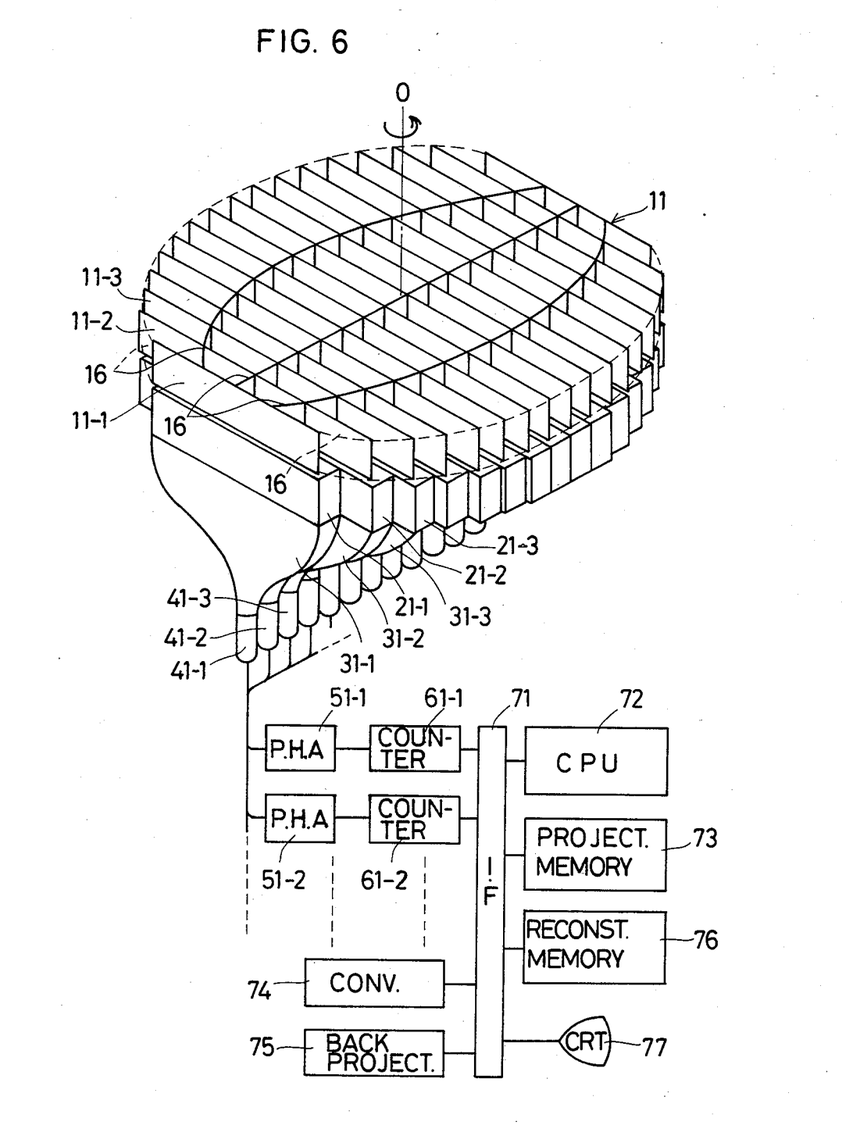
FIG. 6 is a schematic block diagram of an embodiment of the present invention.

In FIG. 6, a plurality of long and slender scintillators 21-1, 21-2, 21-3, . . . are arranged so as to allow their longitudinal edges to abut on each other and so as to be shaped like a flat disk as a whole. Light emitted by the scintillators 21-1, 21-2, 21-3, . . . , which is position independent in the lengthwise direction of the scintillators, is fed to photoelectric converters such as photomultipliers (PMT) 41-1, 41-2, 41-3, . . . through light guides 31-1, 31-2, 31-3, . . . , respectively, which consist of optical fibers or the like. A parallel plate collimator 11 for restricting gamma rays which are incoming perpendicularly to the longitudinal edges of each scintillator is provided on the front sides of the scintillators 21-1, 21-2, 21-3, . . . The collimator 11 consists of a first set of shielding plates 11-1, 11-2, 11-3, . . . arranged in parallel with each other and a second set of shielding plates 16 disposed at both ends and in the middle portion of the first set of shielding plates so as to intersect them and adapted to restrict, to some extent, gamma rays which are incoming parallel to the longitudinal edges of each scintillator. The scintillators 21-1, 21-2, 21-3, . . . , together with the collimator 11, are adapted to be revolved about the 0 axis either by 180° or by 360°.

Figure 7:
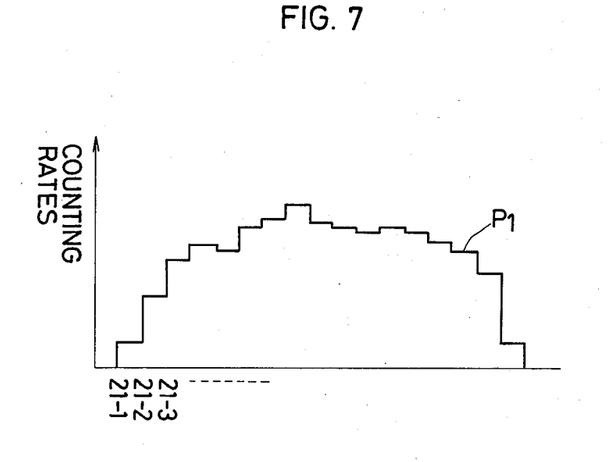
FIG. 7 is a graphical representation of data collected while the rotatable collimator is at a standstill in an angular position.

Let it be supposed that, in an angular position, gamma rays emitted from RI are admitted into the scintillators 21-1, 21-2, 21-3, . . . through the spaces left between the first set of shielding plates 11-1, 11-2, 11-3, . . . of the collimator 11. Then, pulse signals which correspond to the energy of the incident gamma rays are generated from PMT 41-1, 41-2, 41-3, . . . and discriminated by pulse height analyzers 51-1, 51-2, . . . so that signals which correspond to the gamma rays incident on the prescribed energy windows may be detected. The signals thus detected are enumerated by counters 61-1, 61-2, . . . Such enumeration is carried out by the counters 61-1, 61-2, . . . for the predetermined length of time during which the scintillator and rotatable collimator assembly is at a standstill in each angular position. Thus a large number of outputs are taken from these counters at a time in the form of discrete values. A data $P_1$ in the form of a histogram as shown in FIG. 7 is obtained by arranging these discrete values in the same order as that in which the scintillators 21-1, 21-2, 21-3, . . . are arranged. The data $P_1$, after passage through an interface 71, is written in a memory 73 under the control of a central processing unit (CPU) 72. Such writing, which is followed by the resetting of the counters 61-1, 61-2, . . . , is repeated every time the scintillators 21-1, 21-2, 21-3, . . . and the collimator 11 have rotated by a very small angle. Thus a large number of data $P_1$, $P_2$, $P_3$, . . . , $P_m$, the first of which is shown in FIG. 7, are obtained from all the angular positions and stored in the memory 73.

When such data have been collected, they are taken out of the memory 73 and subjected to operation for image reconstruction. In this embodiment, convolution and backprojection is used as an algorithm for image reconstruction. The selection of this algorithm will be justified because, since each of the data $P_1$, $P_2$, $P_3$, . . . , $P_m$ represents a distribution of the discrete values obtained in each angular position by integrating the number of incident gamma rays in the lengthwise direction of the scintillators, to process these data for the reconstruction of an image which represents a distribution of RI is tantamount to mathematically reconstructing an original image from a plurality of projections in computer tomography. For this reason, other techniques such as the method of successive approximation may be used in the alternative. As shown in FIG. 6, however, it is presently preferred that convolution is carried out by a convolver 74 in the first place and then back projection is carried out by a back projector 75 so that the image, which represents a distribution of RI, may be written in an image memory 76, reconstructed therein as one which consists, e.g., of 256×256 matrix, and displayed by a display unit such as a CRT 77.

Figure 8:
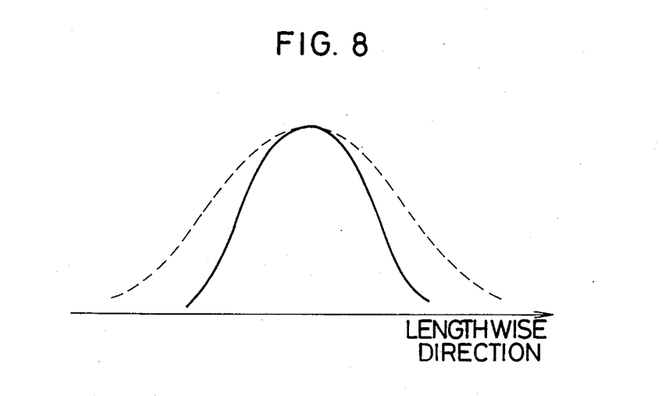
FIG. 8 is a graphical representation illustrating how the distribution of counting rates obtained in the lengthwise direction of each scintillator differently shows itself according to whether or not the shields are disposed.

For the above-mentioned image reconstruction per se, the collimators have only to restrict gamma rays which are incoming perpendicularly to the longitudinal edges of each scintillator. However, if the embodiment shown in FIG. 6 is devoid of the second set of shielding plates 16 and consequently the gamma rays which are incoming in the lengthwise direction of the scintillators are not restricted at all, the distribution of counting rates obtained in the lengthwise direction of each scintillator will show itself in the form of a prolate curve as shown in FIG. 8 with a broken curve. In view of the known fact that both end portions of a scintillator are characterized by extremely low counting rates and low sensitivity, the above-mentioned prolate curve may be regarded as indicating that a scintillator which is devoid of the second set of shielding plates 16 has an especially wide range of low-sensitivity end portions and is apt to produce an artefact or narrow the effective visual field. Especially, if the second set of shielding plates 16 are not provided at both ends of the first set of shielding plates 11-1, 11-2, 11-3, . . . , gamma rays incident on the scintillators from the exterior of the visual field will constitute a major cause of an artefact. According to the present invention, the second set of shielding plates 16 are disposed at both ends and in the middle portion of the first set of shielding plates 11-1, 11-2, 11-3, . . . as shown in FIG. 6 so that gamma rays which are incoming in the lengthwise direction of the scintillators may be restricted. Consequently the distribution of counting rates obtained in the lengthwise direction of each scintillator shows itself in the form of a comparatively oblate curve as shown in FIG. 8 with a solid curve, which indicates a narrow range of low sensitivity end portions and a wide area of effective visual field. The shielding plates 16 provided on the circumference of the scintillator assembly serve to prevent the incidence of gamma rays from the exterior of the visual field.

In the above-described embodiment of the present invention, a plurality of long and slender scintillators 21-1, 21-2, 21-3, . . . are used for integrating the number of incident gamma rays in the lengthwise direction of the first set of shielding plates 11-1, 11-2, 11-3, . . . of the parallel plate collimator 11 and for collecting data on the distribution of these integrated counting rates in the direction perpendicular to the longitudinal edges of the first set of shielding plates 11-1, 11-2, 11-3, . . . It should be borne in mind, however, that the long and slender scintillators are not exhaustive of the forms which may be taken by a radiation detector. The radiation detector may take any other forms so long as they allow the above-mentioned distribution to be found. Furthermore, although the scintillators and collimator in the above-described embodiment of the present invention are shaped like a disk as a whole, it goes without saying that they may be rectangularly shaped.

Figure 9:
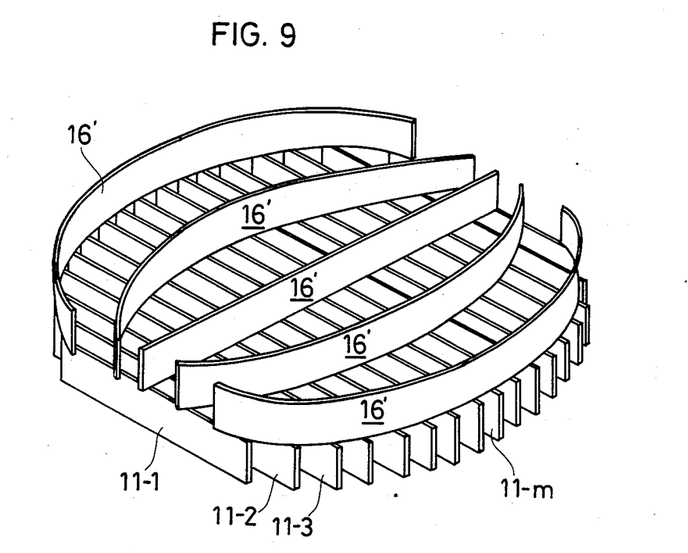
FIG. 9 is a view illustrating an embodiment of the collimator and shields according to the present invention.

In order to make the shielding highly effective, the second set of shielding plates 16' are preferably disposed in such a manner that their lower edges abut against the upper edges of the first set of shielding plates 11-1, 11-2, 11-3, . . . of the collimator 11 so as to form solid crossings as shown in FIG. 9.

The second collimator need not be round shaped but it may be coarse parallel plates in such a manner that the first and the second parallel plates form a right angled lattice.

Figure 10:
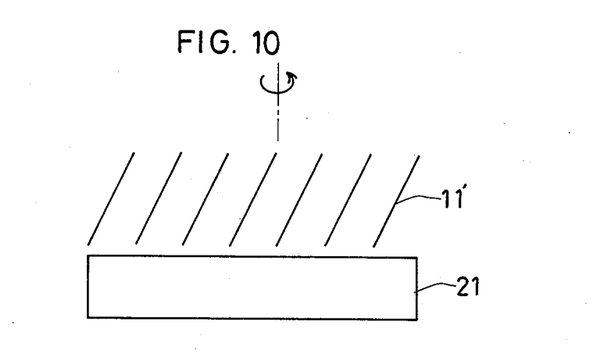
FIG. 10 is a view illustrating an embodiment of the collimator according to the present invention.

The parallel plate collimator need not necessarily make a right angle with the upper surface of each scintillator, but may be inclined (e.g., at 60°) as shown by the numeral 11' in FIG. 10. In this case, data can be obtained in the course of 360-degree rotation and a longitudinal tomogram can be obtained in any depth.

Figure 11:
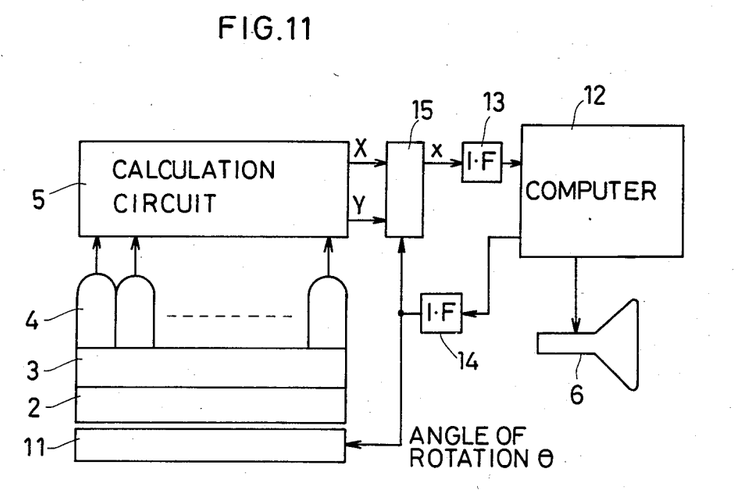
FIG. 11 is a schematic block diagram of still another embodiment of the present invention.
Figure 12:
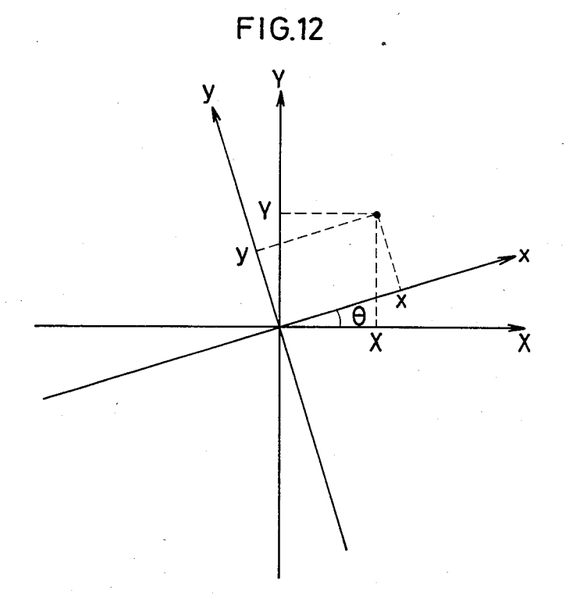
FIG. 12 is a drawing to help explain how the coordinate transformation may be effected in accordance with the teachings of the present invention.

Reference is now specifically made to an embodiment shown in FIGS. 11 and 12. This embodiment is designed for accomplishing the second object of the present invention.

This embodiment, which bears some resemblance to the construction of a conventional scintillation camera shown in FIG. 4, differs therefrom in that the collimator 11 shown in FIGS. 6 or 9 is used and that a coordinate transformation circuit 15 is interposed between the position calculation circuit 5 and the interface circuit 13. By the coordinate transformation circuit 15, the XY coordinates of the position calculation circuit 5 are transformed into xy coordinates which represent the position occupied by the XY coordinates of the collimator 11 when it has rotated by a predetermined angle. Coordinate transformation is carried out as shown in FIG. 12 in accordance with the following formulas in the coordinate transformation circuit 15 upon receipt of a signal from the computer 12 which indicates the angle of rotation $\theta$:

$$x = X \cos \theta + Y \sin \theta$$

$$y = Y \cos \theta - X \sin \theta$$

The signal y is neglected (i.e., either fixed in the coordinate transformation circuit or prevented from being fed out therefrom), and only the signal x is fed to a memory location in the computer 12 which is allotted for each point of incidence of a radioactive ray. The signals x are fed to the memory locations in this manner and are enumerated in the direction of the x axis, which is at an angular distance of $\theta$ from the X axis, so that data on one-dimensional distribution in that direction may be obtained. This procedure is repeated at various angular distances from the X axis in the course of 180- or 360-degree rotation so that all the data required for image reconstruction may be collected.

The above-described construction serves to simplify the computer operation, because the provision of a coordinate transformation circuit 15 allows automatic addition to be carried out in each memory location. Because coordinate transformation takes place in real-time, the time interval from the instant the operation is started until the instant the data on one-dimensional distribution is obtained can be reduced and consequently an image can be quickly delivered. Above all things, it is noteworthy that a drastically smaller number of memory locations suffice for the collection of data. For example, let it be supposed that data are going to be collected with the one-dimensional density of picture elements and the number of angular positions of the collimator being equal to those presupposed for the above-mentioned two-dimensional matrix. The number of memory locations required for the collection of data is only 512×360 in which is 1/512 as many as the number of memory locations required for the conventional two-dimensional matrix.

Figure 13:
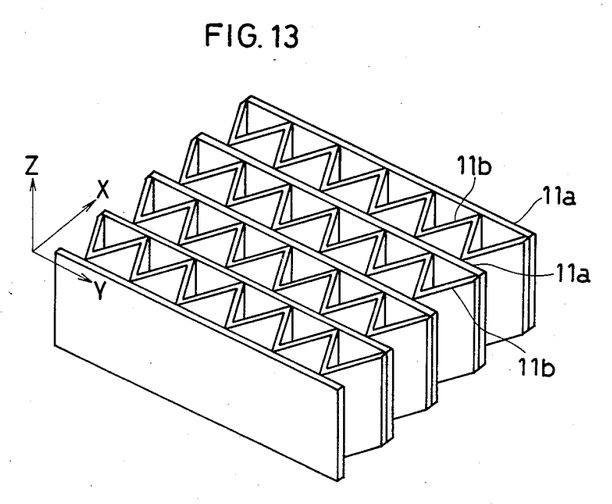
FIG. 13 is a perspective view of parallel plate collimator according to the present invention.
Figure 14:
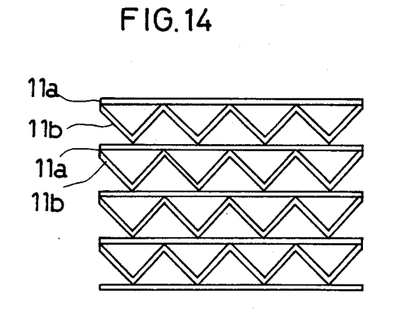
FIG. 14 is a plan view thereof.
Figure 15:
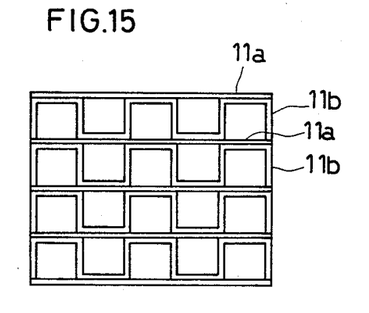
FIG. 15 is a plan view of another parallel plate collimator according to the present invention.

Reference is now specifically made to an embodiment shown in FIGS. 13 to 15. This embodiment is designed for accomplishing the third object of the present invention.

As shown in FIGS. 13 and 14, a plurality of plates 11a are arranged so as to be equally spaced perpendicularly to the X axis. A corrugated member 11b is inserted as a spacer into each space between adjacent plates 11a and unified therewith by means of an adhesive agent or the like. The plates 11a are made of a material such as lead, so that they have an excellent property of absorbing gamma rays. The members 11b are made, e.g., of an iron or copper sheet, which is inferior to the plates 11a in the property of absorbing gamma rays, or of a polyester sheet, which hardly absorbs gamma rays and has excellent penetrability.

Although each corrugated member 11b shown in FIGS. 13 and 14 forms triangular openings in combination with adjacent plates 11a, the triangle is not exhaustive of the forms which may be taken by these openings. They may be square as shown in FIG. 15 so long as their axes run parallel with the Z axis.

Figure 16:
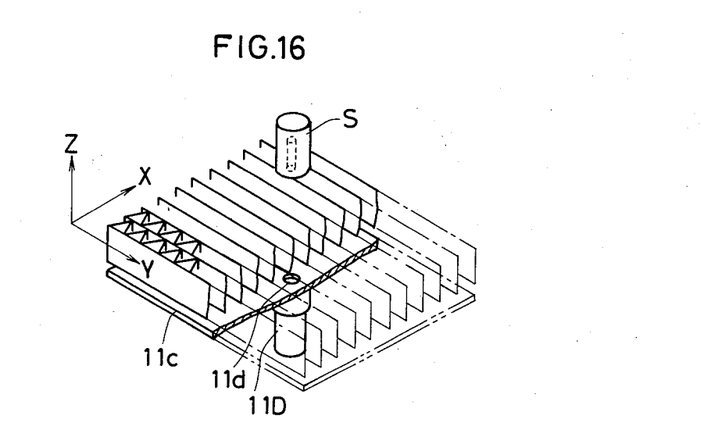
FIG. 16 is a partially cutaway schematic perspective view to help explain how to measure the effects of the collimators as a field stop.
Figure 17:
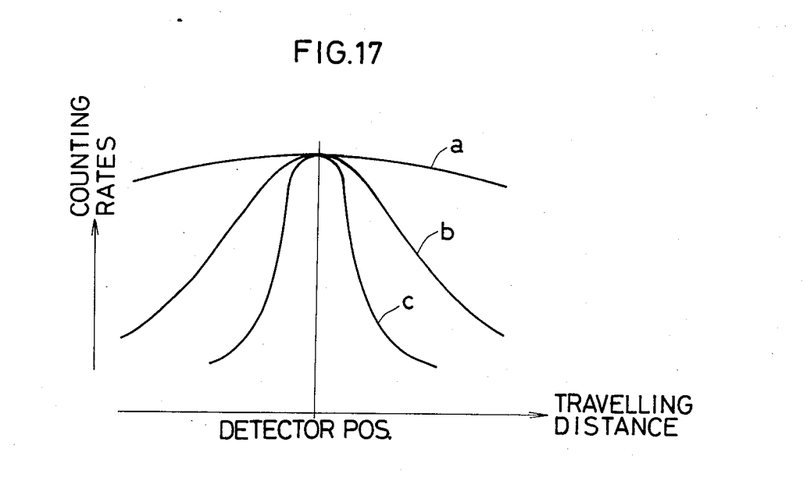
FIG. 17 is a graphical representation of the distributions of counting rates which indicate the abovementioned effects.

Reference is now specifically made to the effects of the above-described collimator as a field stop. FIG. 16 helps explain how to evaluate such effects. A lead plate 11c provided with a pinhole 11d is disposed under the collimator of the type shown in FIGS. 13 and 14 (or in FIG. 15). A miniature radiation detector 11D is disposed substantially under the pinhole 11d. A radioactive source S, which is disposed over the collimator, is moved in the directions of the X and Y axes so that the counting rates per unit time may be measured. Distribution curves as shown in FIG. 17 are obtained when the counting rates found in a direction are plotted on an ordinate against the traveling distance of the radioactive source on an abscissa. Curves a and b show the distributions of counting rates measured in the direction of the Y axis with polyester films and iron sheets respectively used as the members 11b. The distribution of counting rates measured in the direction of the X axis, which is shown by the curve c, is unrelated to the material of which the members 11b are made. The implication of the curves a and c is that polyester films hardly have an effect as a field stop in the direction of the Y axis although they have the effect in the direction of the X axis. The implication of the curve b is that the effect of the iron sheets in the direction of the Y axis stands midway between the effects of the iron sheets and the polyester films in the direction of the X axis. Thus the collimator is allowed to have any degree of anisotropy. The degree depends on whether a material having a pronounced or slight property of absorbing gamma rays is used for the corrugated members 11b.

From the foregoing, it will be apparent that the present invention provides a collimator of simplified construction for ease of manufacture, which is derived from the facts that the corrugated members can be easily manufactured with high accuracy and that they serve both as spacers and as an anisotropic field stop. Gamma rays which are incoming in the direction of the Z axis do not undergo attenuation, because they are not absorbed by the corrugated members.

What is claimed is:

1. A scintillation camera comprising:
   a radiation detector provided with scintillators for producing scintillations of light in response to detected radiation;
   a parallel plate collimator rotatably disposed on the front side of said radiation detector and comprising a first set of shielding plates equally spaced in parallel with each other;
   means, including a position calculation circuit, responsive to scintillations of light for calculating position signals representing data on two-dimensional distribution of said scintillations;
   a coordinate transformation circuit responsive to said position signals for producing, each time said collimator is rotated by a predetermined angle, signals representing data on one-dimensional distribution; and,
   means responsive to said signals representing data on one-dimensional distribution for reconstructing an image.

2. A scintillation camera as claimed in claim 1 wherein said collimator further comprises a second set of shielding plates disposed transverse to said first set.

3. A scintillation camera as claimed in claim 2 wherein the shielding plates of said second set are fewer in number and spaced further apart than the shielding plates of said first set.

4. A scintillation camera as claimed in claim 2 wherein the shielding plates of said first and second sets lie in the same plane.

5. A scintillation camera as claimed in claim 1 wherein said collimator further comprises a second set of shielding plates disposed transverse to said first set, the shielding plates of said first and second sets being disposed in separate parallel planes with the lower edges of the plates of said second set abutting the upper edges of the plates of said first set.

6. A scintillation camera as claimed in claim 5 wherein the shielding plates of said second set are spaced further apart than the shielding plates of said first set.

7. A scintillation camera as claimed in claim 1 wherein said coordinate transformation circuit includes means for solving the equation:

$$x = X \cos \theta + Y \sin \theta$$

where $\theta$ is the total angle through which the collimator has been rotated and x represents the data on one-dimensional distribution.

8. A scintillation camera as claimed in claim 7 wherein said arithmetic means includes memory means for storing the values x.

* * * * *